United States Patent [19]

Dempski et al.

[11] 4,404,193

[45] Sep. 13, 1983

[54] METHYLDOPA COMPOSITION

[75] Inventors: Robert E. Dempski, Dresher; Joseph L. O'Neill, Lansdale, both of Pa.

[73] Assignee: Merck & Co., Inc., Rahway, N.J.

[21] Appl. No.: 309,956

[22] Filed: Oct. 9, 1981

Related U.S. Application Data

[63] Continuation-in-part of Ser. No. 965,462, Dec. 1, 1978, abandoned.

[51] Int. Cl.³ .................. A61K 31/195; A61K 31/715
[52] U.S. Cl. ..................................... 424/176; 424/180; 424/319
[58] Field of Search ............................... 424/319, 176

[56] References Cited

U.S. PATENT DOCUMENTS 3,230,143  1/1966  Marcus .
3,526,698  9/1970  Polli et al. ........................... 424/175
3,976,782  8/1976  Saari .................................... 424/319
4,029,773  6/1977  Beigler et al. ....................... 424/180

FOREIGN PATENT DOCUMENTS 957586  5/1964  United Kingdom .

OTHER PUBLICATIONS

The United States Pharmacopeia pp. 678–680, 629–693, 706, (1970).
C & E News, pp. 59–69 (Feb. 24, 1958).
Hospital Formulary 24:08 (1966).
Newton, D. et al., Am. J. Hosp. Pharm. 32, 817–821 (1975).

*Primary Examiner*—Richard A. Schwartz
*Attorney, Agent, or Firm*—Alice O. Robertson; Daniel T. Szura

[57] ABSTRACT

An aqueous suspension containing methyldopa and sucrose is disclosed. This composition is an oral dosage form for treating hypertension that is bioavailable.

4 Claims, No Drawings

METHYLDOPA COMPOSITION

CROSS REFERENCE TO RELATED APPLICATIONS

This application is a continuation-in-part of U.S. application Ser. No. 965,462 filed Dec. 1, 1978, now abandoned.

BACKGROUND OF THE INVENTION

The present invention concerns a liquid suspension containing methyldopa useful for oral treatment of hypertension.

Methyldopa (L-3-(3,4-dihydroxyphenyl)-2-methylalanine) is a known antihypertensive agent. It is generally administered orally for treating a hypertensive patient. The dosage form commonly used is a tablet. In some instances e.g. with children or the very elderly, administration of methyldopa in a palatable, liquid dosage form would be advantageous provided that it had a bioavailability at least equivalent to that of the tablet form.

Such a liquid pharmaceutical composition containing methyldopa has been discovered.

SUMMARY OF THE INVENTION

A liquid pharmaceutical composition for treating hypertension containing methyldopa and sucrose.

DESCRIPTION OF THE PREFERRED EMBODIMENTS

An embodiment of the present invention is a pharmaceutical composition for treating hypertension in humans comprising an aqueous suspension containing methyldopa and sucrose.

This suspension can contain from about 15 mg to about 100 mg of methyldopa per milliter (ml) of aqueous suspension. It will preferably contain from 25 mg. to 100 mg. of methyldopa, and most preferably about 50 mg. of methyldopa, per ml. of said suspension.

The suspension must also contain from about 1 mg. to about 24 mg. of sucrose per mg. of methyldopa. Preferably, the suspension will contain from about 1 mg. to about 12 mg. of sucrose per mg. of methyldopa; more preferably the weight ratio of methyldopa:sucrose is about 1:2 to about 1:10 and most preferably about 1:10.

In addition to the essential ingredients, methyldopa and sucrose, the composition of the present invention can contain other ingredients conventionally used to prepare a pharmaceutically useful suspension. Such ingredients include antioxidants, e.g. sodium bisulfite, disodium edetate and citric acid, thickening/suspending agents, e.g. xanthan gum and Veegum K, flavorings, preservatives, coloring agents and the like. Conventional procedures and equipment are used to prepare the present suspensions.

An outstanding characteristic of the present suspension is that the bioavailability of the methyldopa is equal to or greater than methyldopa administered in conventional tablet form. When sorbitol, which is very commonly used to prepare pharmaceutically useful suspensions, is substituted for the sucrose in the present suspension, the bioavailability of the methyldopa is substantially less than methyldopa administered as a tablet. This is indeed surprising since sorbitol is reported to enhance the bioavailability of other pharmaceutically active compounds such as vitamins, (C & E, News, p. 59-60, February 24, 1958).

The bioavailability of methyldopa was determined in vivo by measuring the concentration of methyldopa and conjugated methyldopa in the plasma and urine of humans subjects to whom 500 mg of methyldopa were administed in standard tablet form and in suspension form. The suspension and standard tablet formulations (A, B & C) and bioavailability data are presented in the following tables:

TABLE I
METHYLDOPA FORMULATIONS A, B, & C

| Ingredients | A<br>Sorbitol<br>Suspension<br>mg/ml | B<br>Sucrose<br>Suspension<br>mg/ml |
|---|---|---|
| Methyldopa Anhydrous | 50 | 50 |
| Keltrol | 3 | — |
| Avicel RC-591 | — | 10 |
| Ethyl Alcohol | 0.0116 ml | 0.0116 ml |
| Disodium Edetate | 0.5 | 0.5 |
| Sodium Bisulfite | 2 | 2 |
| Citric Acid | 1 | 1 |
| Polysorbate 80 | 0.2 | 0.2 |
| Orange Flavor | 0.004 ml | 0.004 ml |
| Pineapple Flavor | 0.002 ml | 0.002 ml |
| Preservatives | 1-1.4 | 1-1.4 |
| Sorbital Solution 70% | 0.73 ml | — |
| Sucrose | — | 500 |
| Purified water qsad | 1 ml | 1 ml |

| Ingredients | C<br>Standard Tablet |
|---|---|
| Methyldopa | 250 mg. |
| Acid Citric Anhyd. No. 80 Powder USP | 4.3 mg. |
| Calcium Disodium Edetate USP | 0.2 mg. |
| Ethyl Cellulose NF N 100 | 20.0 mg. |
| Ethyl Cellulose NF N 100<br>(as 8% solution in 20620 Alcohol AS3A anhydrous) | 6.16 mg. |
| Alcohol SD3A Anhydrous | — |
| Guar Gum Jaguar A-20-B | 15.0 mg. |
| Solka Floc Dev 2030 | 12.0 mg. |
| Cab-O-Sil M-5 | 2.0 mg. |
| Magnesium Stearate USP | 1.43 mg. |
| Pre-Coating | Per Tablet |
| Hydroxypropyl Methylcellulose NF 50 cps | 1.25 mg. |
| Diethyl Phthalate | 0.30 mg. |

TABLE II
Bioavailability Data

| A. Urinary | [a]Mean urinary recovery. Total 0–36 hours - α methyldopa plus conjugate in mg |
|---|---|
| Standard Tablet C | 151 |
| Sorbitol Composition A | 73.4 |
| Sucrose Composition B | 192 |

| B. Plasma Concentrations | [b]Mean plasma concentrations at 4 hours - α methyldopa plus conjugate in mcg/ml |
|---|---|
| Standard Tablet C | 4.02 |
| Sorbitol Composition A | 2.09 |
| Sucrose Composition B | 4.51 |

[a]Data from nine human subjects after administration of a 500 mg dose of methyldopa in either tablet or suspension form in crossover studies.
[b]Data from nine human subjects after administration of a 500 mg dose of methyldopa in either tablet or suspension form in crossover studies.

These measurements (in Table II) show the bioavailability of methyldopa in the suspension containing sucrose form is superior to the tablet or suspension containing sorbitol forms.

Following are formulations illustrating the compositions of the present invention:

| Ingredient | SUSPENSIONS FORMULATIONS | | | | | | | |
|---|---|---|---|---|---|---|---|---|
| | I | | II | | III | | IV | |
| Methyldopa USP Milled (Anhydrous) | 50.0 | mg. | 50.0 | mg. | 100 | mg. | 100 | mg. |
| Microcrystalline Cellulose and Sodium Carboxymethylcellulose NF (Avicel RC591 NF) | 10.0 | mg. | 10.0 | mg. | 10.0 | mg. | 10.0 | mg. |
| Disodium Edetate USP | 0.50 | mg. | 0.50 | mg. | 0.50 | mg. | 0.50 | mg. |
| Sodium Bisulfite USP | 2.00 | mg. | 2.00 | mg. | 2.00 | mg. | 2.00 | mg. |
| Citric Acid Monohydrate | 1.00 | mg. | 1.00 | mg. | 1.00 | mg. | 1.00 | mg. |
| Sugar USP Med. Gran. | 500 | mg. | 200 | mg. | 500 | mg. | 200 | mg. |
| Glycerin USP | 10.0 | mg. | 10.0 | mg. | 10.0 | mg. | 10.0 | mg. |
| Ethyl Alcohol USP 95% | 0.011 | ml. | 0.011 | ml. | 0.011 | ml. | 0.011 | ml. |
| Polysorbate 80 USP | 0.20 | mg. | 0.20 | mg. | 0.20 | mg. | 0.20 | mg. |
| Benzoic Acid | 1.00 | mg. | 1.00 | mg. | 1.00 | mg. | 1.00 | mg. |
| Orange Flavor Comp. Fritzsche Dodge & Olcott 16242 | 0.0004 | ml. | 0.0004 | ml. | 0.0004 | ml. | 0.0004 | ml. |
| Pineapple Art. Flavor Fritzsche Dodge & Olcott 05194 | 0.0002 | ml. | 0.0002 | ml | 0.0002 | ml. | 0.0002 | ml. |
| Water Purified USP q.s. | 1.0 | ml. | 1.0 | ml. | 1.0 | ml. | 1.0 | ml. |

What is claimed is:

1. A pharmaceutical composition for the oral treatment of hypertension comprising an aqueous suspension containing about 50 mg of methyldopa per ml of said suspension, about 500 mg of sucrose per ml of said suspension such that the weight ratio of methyldopa:sucrose is about 1:10.

2. The composition of claim 1 which is characterized by having bioequivalence equal or superior to a tablet containing an equivalent amount of methyldopa.

3. The composition of claim 1 wherein said aqueous suspension consists essentially of the following formulation:

| | |
|---|---|
| Methyldopa Anhydrous | 50 mg |
| Avicel RC-591 | 10 mg |
| Ethyl Alcohol (95%) | 0.011 ml |
| Disodium Edetate | 0.5 mg |
| Sodium Bisulfite | 2 mg |
| Citric Acid | 1 mg |
| Polysorbate 80 | 0.2 mg |
| Preservatives | 1-1.4 mg |
| Sucrose | 500 mg |
| Purified water qsad | 1 ml |

4. The composition of claim 3 having bioequivalence superior to a tablet containing an equivalent amount of methyldopa.

* * * * *